March 1, 1955 D. AICARDI Plant Pat. 1,355
ROSE PLANT
Filed May 8, 1953
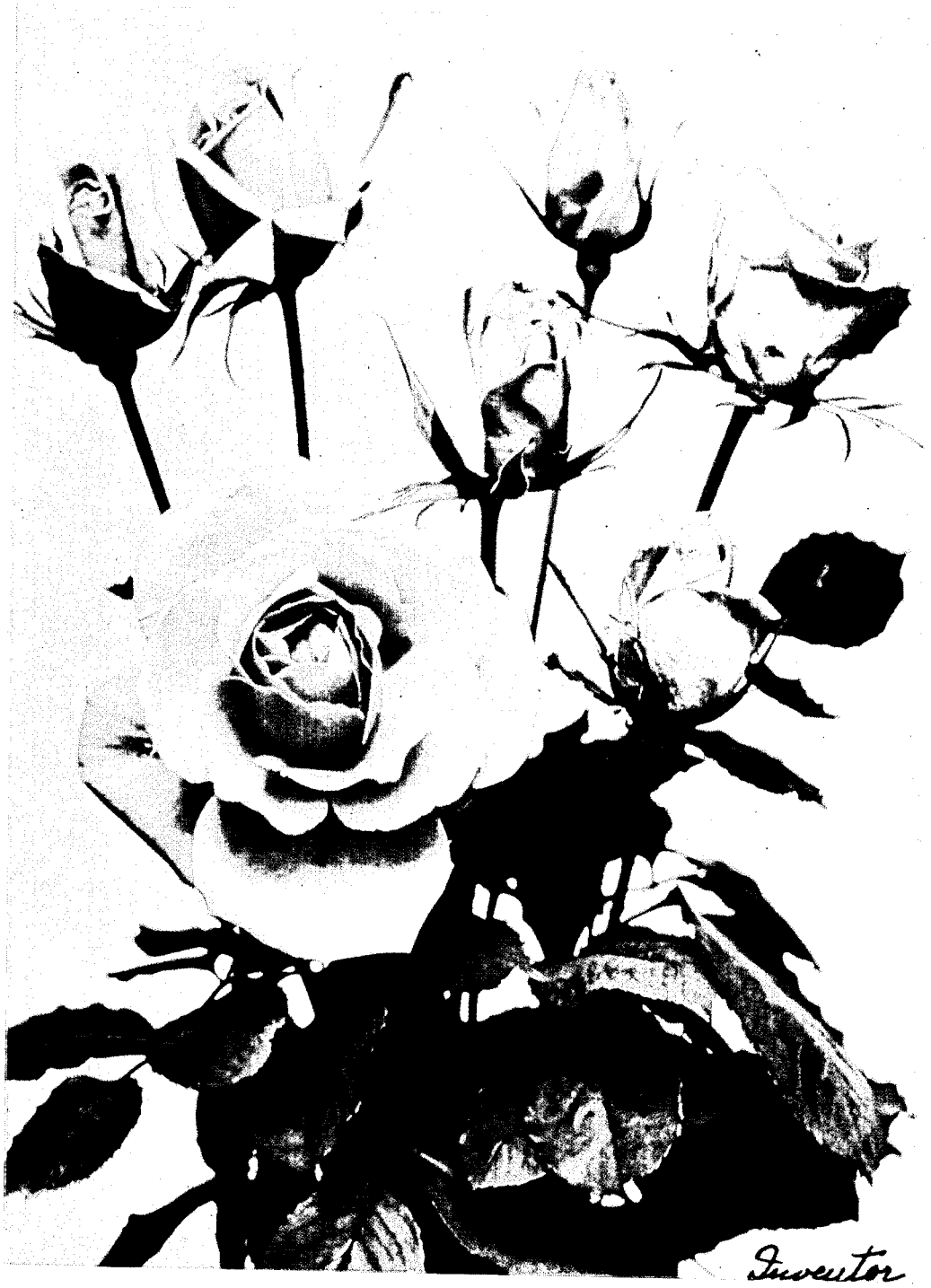
Inventor
D. Aicardi
By: Robb & Robb
Attorneys.

United States Patent Office

Plant Pat. 1,355
Patented Mar. 1, 1955

1,355

ROSE PLANT

Domenico Aicardi, San Remo, Italy, assignor to Vincenzo Asseretto, San Remo, Italy Application May 8, 1953, Serial No. 353,926

Claims priority, application Italy May 12, 1952

1 Claim. (Cl. 47—61)

The present invention relates to a new and distinct variety of rose plant of the hybrid tea class, which was originated by me by crossing the variety "Julien Potin" (unpatented) with the variety "Sensation" (unpatented).

The primary objective in making this cross was to produce a new variety of rose plant having flowers of Lilac Rose color, combined with other improved characteristics which make the new variety especially suitable and desirable for the cut-flower industry, as well as for garden decoration. This objective was fully achieved, as evidenced by the fact that my new variety produces large-sized flowers of Lilac Rose general color tonality, combined with exceptional hardiness, recurrency of bloom and vigorous growth.

The foregoing characteristics definitely distinguish my new variety from its parents, as well as from all other varieties of its class, and make the same particularly useful for industrial culture under glass, as well as for outdoor use.

In comparison with its parents, the new variety is particularly distinguished by its attractive Lilac Rose color which is quite different from the color of the flowers of either parent. The flowers of the variety "Sensation" are normally Scarlet Crimson in color, whereas those of "Julien Potin" are clear yellow in color. In its general habits, my new variety more nearly resembles the variety "Sensation," but has larger leaves. Likewise, the form of the flowers of my new variety somewhat resembles that of "Sensation," but the flowers of my new variety particularly differ from both parents by maintaining their cupped shape, even when fully open.

Asexual reproduction of my new variety by budding at San Remo, Italy, shows that the foregoing characteristics and distinctions come true to form and are established and transmitted through succeeding propagations.

The accompanying drawing shows typical specimens of the flowers, foliage and stems of my new variety in different stages of development.

The following is a detailed description of the new variety, with color terminology in accordance with the French Repertoire Des Couleurs by Rene Oberthur, issued by the Societe Francaise Des Chrysanthemistes (1905 Standard Edition), except where general color terms of ordinary dictionary significance are obvious:

Parentage: "Julien Potin"×"Sensation."
Classification:
*Botanic.*—Hybrid tea.
*Commercial.*—Hybrid tea.

FLOWER (Observations made from plants grown in a nursery at San Remo, Italy)

Blooming habit: Recurrent—continuous.
Bud:
*Size.*—Large.
*Form.*—Triangular; long-pointed.
*Color.*—When sepals first divide—Mauve Rose, Tab. 153/1–2–3. When sepals begin to unfurl—Lilac Rose, Tab. 152/1–2–3. When half blown—Lilac Rose, Tab. 152/1–2–3. Inside of petals—Lilac Rose, Tab. 152/1–2–3. Reverse of petals—Mauve Rose, Tab. 153/1–2–3.
*Sepals.*—Very long, with velvety surface.
*Calyx.*—Shape—funnel. Size—large. Aspect—smooth. Strength—erect. Color—Verdant Green, Tab. 268/1–2–3.

*Opening.*—Opens freely, even under adverse weather conditions.
Bloom:
*Size.*—Large; from 15 to 18 cm. in diameter when fully open.
*Borne.*—Singly.
*Stems.*—Long; thin; hard; strong.
*Form.*—Cup-shaped.
*Petalage.*—Very double; about 30 to 40 petals under usual conditions.
*Color.*—Center of flower—Lilac Rose, Tab. 152/1–2. Outer petals—Lilac Rose, Tab. 152/1–2–3. Base of petals—small yellow spot. Inside of petals—Lilac Rose, Tab. 152/1–2–3. Reverse of petals—Mauve Rose, Tab. 153/1–2–3. General tonality from a distance—Lilac Rose, Tab. 152/1–2–3.
*Variegations.*—None.
*Discoloration.*—None.
Petals:
*Texture.*—Thick; resistant to adverse weather conditions.
*Appearance.*—Inside—satiny. Outside—satiny.
*Form.*—Round to oval.
*Arrangement.*—Imbricated (shingle-like).
*Petaloids in center.*—Few; like little stamens.
*Persistence.*—Durable.
*Fragrance.*—Sweet-scented. Nature—centifolia.
*Lasting quality.*—Very long, even after the flower has been cut.

REPRODUCTIVE ORGANS

Stamens: Very numerous; separated.
Anthers: Well-expanded. Color—Golden Yellow (Tab. 26/1–2).
Threads: Very long.
Pollen: Not always present. Color—Lemon Yellow when present (Tab. 21/1–2–3).
Styles: Numerous. Color—greenish white (Tab. 15/1–2–3).
Stigma: Large; well open.
Ovaries: Well-developed; do not protrude from the calyx.
Fruit:
*Form.*—Amphora-shaped (round headed).
*Aspect.*—Smooth.
*Sepals.*—Caducous.
*Color at maturity.*—Reddish-yellow (Tab. 63/1–2–3–4).

PLANT

Form: Bush.
Growth: Very strong; vigorous.
Foliage: Compound of usually 3 or 5, but generally 5 leaflets.
*Size.*—Very large.
*Quantity.*—Abundant.
*Color.*—Upper side—Cypress Green, Tab. 284/3–4. Under side—Dark Grey Green, Tab. 277/1.
*Shape.*—Oval.
*Texture.*—Tender; herbaceous. Upper side—smooth. Under side—smooth.
*Ribs and veins.*—Moderately prominent.
*Edge.*—Moderately serrated.
*Serration.*—Large.
*Rachis.*—Long; thin. Color—upper side—Cypress Green, Tab. 284/3–4; under side—Grey-Green Tab. 277/1).
Wood:
*New wood.*—Color—Dark Grey Green, Tab. 277/2–3, with little stripes of Morocco Red, Tab. 95/2–3.
*Old wood.*—Color—Clear Brownish Green (Tab. 299/1–2).
Thorns:
*Quantity.*—Medium number.
*Form.*—Thick; short.
*Color.*—From greenish white to Morocco Red, Tab. 95/2–3.

*Prickles.*—None.

*Short needles.*—Some on the flower peduncle.

I claim:

A new and distinct variety of rose plant of the hybrid tea class, substantially as herein shown and described, characterized particularly as to novelty by its large-sized flowers of Lilac Rose general color tonality, by its great hardiness and suitability for industrial culture under glass as well as outdoor culture, and by its attractive and continuous blooming habits.

No references cited.